(12) United States Patent
Mertens et al.

(10) Patent No.: US 7,067,108 B2
(45) Date of Patent: Jun. 27, 2006

(54) CHABAZITE-TYPE MOLECULAR SIEVE, ITS SYNTHESIS AND ITS USE IN THE CONVERSION OF OXYGENATES TO OLEFINS

(75) Inventors: Machteld M. Mertens, Boortmeerbeek (BE); Guang Cao, Branchburg, NJ (US); Hailian Li, Sunnyvale, CA (US); Anil S. Guram, San Jose, CA (US); Robert J. Saxton, Pleasanton, CA (US); Mark T. Muraoka, Mountain View, CA (US); Jeffrey C. Yoder, San Jose, CA (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 0 days.

(21) Appl. No.: 11/017,092

(22) Filed: Dec. 20, 2004

(65) Prior Publication Data

US 2005/0197520 A1    Sep. 8, 2005

Related U.S. Application Data

(60) Provisional application No. 60/532,595, filed on Dec. 23, 2003.

(51) Int. Cl.
*C01B 39/48* (2006.01)
*C07C 1/00* (2006.01)

(52) U.S. Cl. .................. 423/709; 423/716; 423/335; 423/DIG. 30; 585/639; 585/640

(58) Field of Classification Search .............. 423/709, 423/716, DIG. 30, 335; 585/639, 640
See application file for complete search history.

(56) References Cited

U.S. PATENT DOCUMENTS 3,030,181 A    4/1962  Milton
4,440,871 A    4/1984  Lok et al. ................. 502/214
4,544,538 A   10/1985  Zones ....................... 423/326
6,079,644 A    6/2000  Linde et al. .................. 241/3
6,207,872 B1 *  3/2001  Barger et al. ............... 585/640
6,620,983 B1 *  9/2003  Cao et al. ................... 585/640
6,773,694 B1 *  8/2004  Lesch et al. ............... 423/709
2002/0038109 A1 *  3/2002  Williams ................... 604/359
2002/0144597 A1 * 10/2002  Olson ........................ 95/143
2003/0069449 A1 *  4/2003  Zones et al. ............... 564/463
2003/0176751 A1    9/2003  Strohmaier et al. ........ 585/639
2005/0101815 A1    5/2005  Xu et al.
2005/0101816 A1    5/2005  Xu et al.
2005/0101817 A1    5/2005  Xu et al.

FOREIGN PATENT DOCUMENTS

| GB | 868846 | 5/1961 |
|----|--------|--------|
| WO | WO 95/05342 | 2/1995 |
| WO | WO 00/06493 | 2/2000 |
| WO | WO 00/06494 | 2/2000 |
| WO | WO 03/078324 | 9/2003 |

OTHER PUBLICATIONS

Diaz-Cabanas, et al, "Synthesis and Structure of Pure $SiO_2$ Chabazite: the $SiO_2$ Polymorph with the Lowest Framework Density", Chem. Commun. 1881 (1998).

J. Baddiley et al., "Chemical Studies in the Biosynthesis of Purine Nucleotides. Part I. The Preparation of N-Glycylglycosylamines," pp. 2818-2823, no date available.

* cited by examiner

*Primary Examiner*—David Sample

(57) ABSTRACT

The synthesis of a crystalline material, in particular a high silica zeolite, having a chabazite-type framework is aided by the addition to the synthesis mixture of seeds of an AEI framework-type material. The chabazite-type product has a relatively small crystal size and exhibits activity and selectivity in the conversion of methanol to lower olefins, especially ethylene and propylene.

57 Claims, 5 Drawing Sheets

CHABAZITE-TYPE MOLECULAR SIEVE, ITS SYNTHESIS AND ITS USE IN THE CONVERSION OF OXYGENATES TO OLEFINS

CROSS REFERENCE TO RELATED APPLICATIONS

This application claims priority to Provisional Application No. 60/532,595, filed Dec. 23, 2003, the disclosures of which are incorporated by reference.

FIELD OF INVENTION

This invention relates to a molecular sieve having a chabazite-type structure, its synthesis and its use in the conversion of oxygenates, particularly methanol, to olefins, particularly ethylene and propylene.

BACKGROUND OF INVENTION

The conversion of oxygenates to olefins (OTO) is currently the subject of intense research because it has the potential for replacing the long-standing steam cracking technology that is today the industry-standard for producing world scale quantities of ethylene and propylene. The very large volumes involved suggest that substantial economic incentives exist for alternate technologies that can deliver high throughputs of light olefins in a cost efficient manner. Whereas steam cracking relies on non-selective thermal reactions of naphtha range hydrocarbons at very high temperatures, OTO exploits catalytic and micro-architectural properties of acidic molecular sieves under milder temperature conditions to produce high yields of ethylene and propylene from methanol.

Current understanding of the OTO reactions suggests a complex sequence in which three major steps can be identified: (1) an induction period leading to the formation of an active carbon pool (alkyl-aromatics), (2) alkylation-dealkylation reactions of these active intermediates leading to products, and (3) a gradual build-up of condensed ring aromatics. OTO is therefore an inherently transient chemical transformation in which the catalyst is in a continuous state of change. The ability of the catalyst to maintain high olefin yields for prolonged periods of time relies on a delicate balance between the relative rates at which the above processes take place. The formation of coke-like molecules is of singular importance because their accumulation interferes with the desired reaction sequence in a number of ways. In particular, coke renders the carbon pool inactive, lowers the rates of diffusion of reactants and products, increases the potential for undesired secondary reactions and limits catalyst life.

Over the last two decades, many catalytic materials have been identified as being useful for carrying out the OTO reactions. Crystalline molecular sieves are the preferred catalysts today because they simultaneously address the acidity and morphological requirements for the reactions. Particularly preferred materials are eight-membered ring aluminosilicates, such as those having the chabazite (CHA) framework type, as well as silicoaluminophosphates of the CHA structure, such as SAPO-34. These molecular sieves have cages that are sufficiently large to accommodate aromatic intermediates while still allowing the diffusional transport of reactants and products into and out of the crystals through regularly interconnected window apertures. By complementing such morphological characteristics with appropriate levels of acid strength and acid density, working catalysts are produced. Extensive research in this area indicates that silicoaluminophosphates are currently more effective OTO catalysts than aluminosilicates. In particular, the control of the silica to alumina molar ratio is a key requirement for the use of aluminosilicates in OTO reactions. Nevertheless, aluminosilicate zeolites continue to be explored for use in OTO and appear to have yet undiscovered potential.

Chabazite is a naturally occurring zeolite with the approximate formula $Ca_6Al_{12}Si_{24}O_{72}$. Three synthetic forms of chabazite are described in "Zeolite Molecular Sieves", by D. W. Breck, published in 1973 by John Wiley & Sons, the complete disclosure of which is incorporated herein by reference. The three synthetic forms reported by Breck are Zeolite "K-G", described in J. Chem. Soc., p. 2822 (1956), Barrer et al; Zeolite D, described in British Patent No. 868,846 (1961); and Zeolite R, described in U.S. Pat. No. 3,030,181 (1962).

U.S. Pat. No. 4,544,538, incorporated herein by reference, describes the synthesis of another synthetic form of chabazite, SSZ-13, using N-alkyl-3-quinuclidinol, N,N,N-trialkyl-1-adamantylammonium cations and/or N,N,N-trialkyl-exoaminonorbornane as a directing agent in a conventional $OH^-$ medium. According to the '538 patent, SSZ-13 typically has a silica to alumina molar ratio of 8 to 50 but it is stated that higher molar ratios can be obtained by varying the relative ratios of the reactants in the synthesis mixture and/or by treating the zeolite with chelating agents or acids to remove aluminum from the zeolite lattice. The '538 patent also discloses that the crystallization of SSZ-13 can be accelerated and the formation of undesirable contaminants can be reduced by adding seeds of SSZ-13 to the synthesis mixture.

According to Published International Application No. WO 00/06494, published Feb. 10, 2000, a colloidal suspension of seeds of the LEV structure can be used to assist in the crystallization of a number of molecular sieve structures, including LEV, FER, MOR, ERI/OFF, MAZ, OFF, ZSM-57 and CHA. Examples of CHA materials are said to include chabazite and the phosphorous containing molecular sieves SAPO-34, ALPO-34, SAPO-37, ALPO-37 and metal containing derivatives thereof.

A silica crystalline molecular sieve having the CHA framework type has been hydrothermally synthesized using N,N,N-trimethyladamantylammonium in hydroxide form as the structure-directing agent at nearly neutral pH in the presence of fluoride. See Diaz-Cabanas, M-J, Barrett, P. A., and Camblor, M. A. "Synthesis and Structure of Pure $SiO_2$ Chabazite: the $SiO_2$ Polymorph with the Lowest Framework Density", Chem. Commun. 1881 (1998).

More recently, an aluminosilicate with the CHA framework type and having a silica to alumina molar ratio in excess of 100, such as from 150 to 2000, has been synthesized in the presence of fluoride ions. See U.S. Patent Application Publication No. 2003/0176751, published Sep. 18, 2003 and incorporated herein by reference.

Existing methods for synthesizing high silica aluminosilicates and all silica molecular sieves with a CHA framework-type have tended to produce materials with a large crystal size. However, small crystal materials are often desirable for catalytic use, especially where a high catalyst surface area is important, such as the conversion of oxygenates to olefins.

U.S. Pat. No. 6,079,644, incorporated herein by reference, describes a zeolite that is identified as SSZ-62 and that has a CHA framework-type and a crystal size of 0.5 micron or less. SSZ-62 is said to have a silica to alumina molar ratio in excess of 10, such as in excess of 30, but the only synthesis example produces a material with a silica to alumina molar ratio of 22.

SUMMARY

In one aspect, the invention resides in a method of synthesizing a crystalline material having a CHA framework-type, the method comprising:
a) forming a reaction mixture capable of forming said crystalline material having a CHA framework-type, wherein the reaction mixture further comprises seeds of a crystalline material comprising an AEI framework-type; and
b) recovering from said reaction mixture said crystalline material comprising a CHA framework-type.

In a further aspect, the invention resides in a method of synthesizing a crystalline material having a CHA framework-type and having, in its calcined and anhydrous form, a composition involving the molar relationship:

$$(n)X_2O_3:YO_2,$$

wherein X is a trivalent element, such as aluminum, boron, iron, indium, and/or gallium; Y is a tetravalent element, such as silicon, tin, titanium and/or germanium; and n is from 0 to less than 0.01, for example from about 0.0005 to about 0.007, such as from about 0.0008 to about 0.005, the method comprising:
(a) preparing a reaction mixture capable of forming said crystalline material having a CHA framework-type, said reaction mixture comprising a source of water, a source of an oxide of the tetravalent element Y, optionally a source of an oxide of the trivalent element X, an organic directing agent for directing the formation of said porous crystalline material and seeds of a crystalline material having a framework-type other than CHA;
(b) maintaining said reaction mixture under conditions sufficient to form crystals of said crystalline material having a CHA framework type; and
(c) recovering said crystalline material from (b).

Conveniently, said seeds comprise a crystalline material having an AEI, LEV, CHA or OFF framework-type, and preferably an AEI framework-type.

Conveniently, said reaction mixture comprises from about 0.1 ppm by weight to about 10,000 ppm by weight, such as from about 100 ppm by weight to about 5,000 by weight, of said seeds.

In one embodiment, said reaction mixture also comprises a halide or a halide-containing compound, such as a fluoride or a fluoride-containing compound.

In one embodiment, said organic directing agent comprises a multi-cyclic amine or ammonium compound. Conveniently, the multi-cyclic amine or ammonium compound comprises a tricyclic or tetracyclic amine or ammonium compound, such as an N-alkyl-3-quinuclidinol, an N,N,N-tri-alkyl-1-adamantylammonium compound, an N,N,N-tri-alkyl-exoaminonorbornane or a combination thereof, such as an N,N,N-trimethyl-1-adamantylammonium compound.

Typically, the crystalline material recovered in (c) is composed of crystals having an average diameter less than or equal to 4 micron, such as from about 0.5 to about 4 micron.

In yet a further aspect, the invention resides in a porous crystalline material having a CHA framework type and having, in its calcined and anhydrous form, a composition involving the molar relationship:

$$(n)X_2O_3:YO_2,$$

wherein X is a trivalent element, Y is a tetravalent element and n is from 0 to less than 0.01, and wherein the crystals of said material have an average diameter less than or equal to 4 micron, such as from about 0.5 to about 4 micron.

In still yet a further aspect, the invention resides in a porous crystalline material having a CHA framework type and having, in its calcined and anhydrous form, a composition involving the molar relationship:

$$(n)X_2O_3:YO_2,$$

wherein X is a trivalent element, Y is a tetravalent element and n is from 0 to less than 0.01, and wherein the crystals of said material are twinned.

Conveniently, the calcined crystalline material contains from about 1 to about 100 ppm, for example from about 5 to about 50 ppm, such as from about 10 to about 20 ppm, by weight of a halide, preferably fluoride.

Conveniently, said porous crystalline material having a CHA framework type is substantially free of framework phosphorus.

In still a further aspect, the invention resides in a process for producing olefins comprising contacting an organic oxygenate compound under oxygenate conversion conditions with a catalyst comprising a porous crystalline material having a CHA framework type as described herein.

It is to be understood that the term "in its calcined, anhydrous form" is used herein to refer to a material which has been heated in air at higher than 400° C. for 0.1 to 10 hours without allowing the material to rehydrate.

In addition, it is to be understood that the term "twinned" crystal is used herein in its commonly accepted sense to mean a crystal which comprises two or more individual single crystals joined together in some definite mutual orientation; the lattice of one individual being related to that of the other individual or individuals in the composite crystal by some simple symmetry operation (see *Essentials of Crystallography* by Duncun Mckie and Christine McKie, Blackwell Scientific Publications, Oxford, 1986. P89.).

DETAILED DESCRIPTION OF THE EMBODIMENTS

Figure 1:
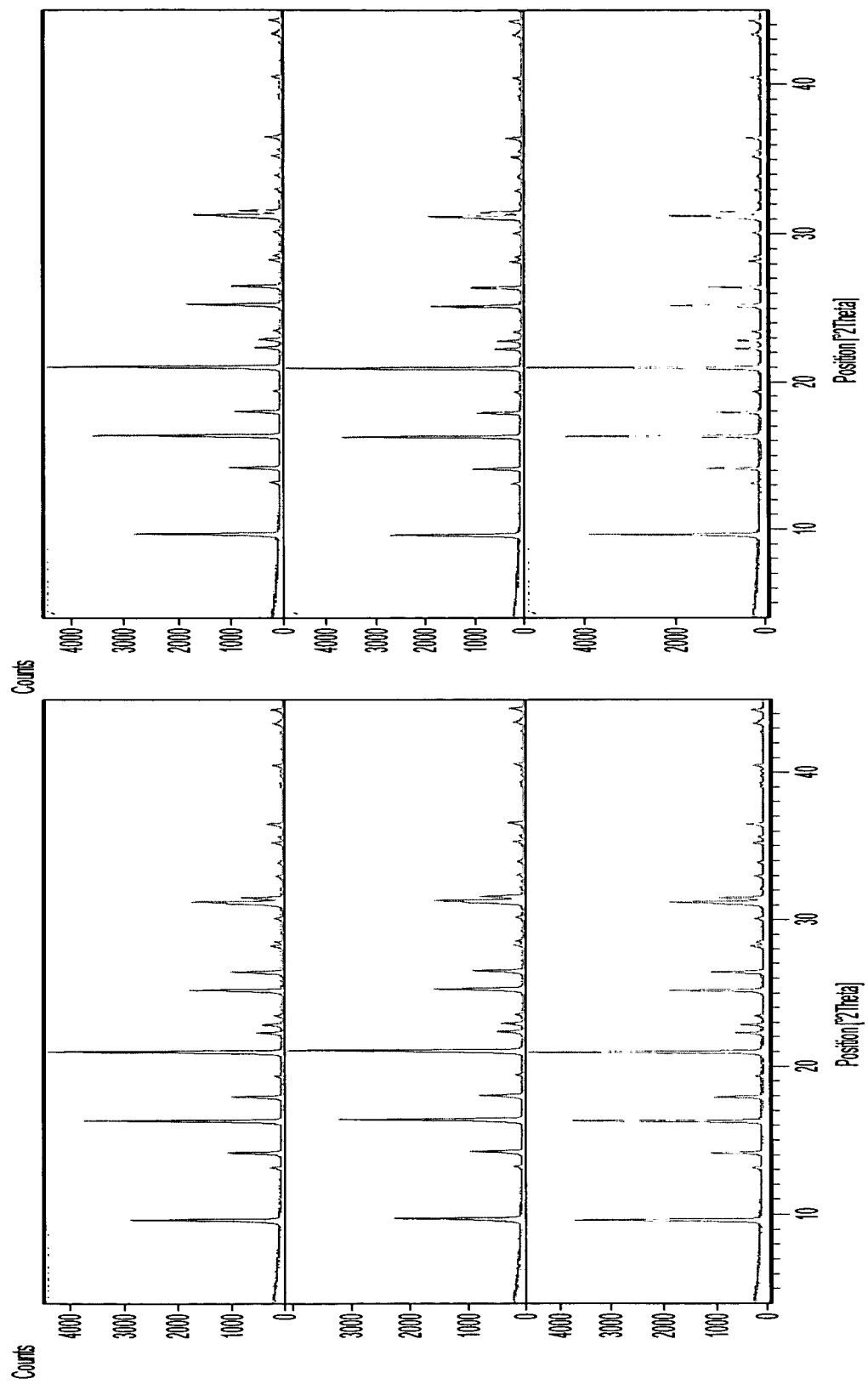
FIGS. 1(a) to 1(f) are X-ray diffraction patterns of the as-synthesized products of the seeded syntheses of Examples 1 to 6 respectively.

The present invention relates to a method of synthesizing a crystalline material, in particular a high silica zeolite, having a chabazite-type framework and to a small crystal form of this material. In addition, the invention relates to the use of this material such as in a process for the conversion of oxygenates, particularly methanol, to olefins, particularly ethylene and propylene.

It is to be appreciated that molecular sieves are classified by the Structure Commission of the International Zeolite Association according to the rules of the IUPAC Commission on Zeolite Nomenclature. According to this classification, framework-type zeolites and other crystalline microporous molecular sieves, for which a structure has been established, are assigned a three letter code and are described in the *Atlas of Zeolite Framework Types*, 5th edition, Elsevier, London, England (2001). Chabazite is one of the molecular sieves for which a structure has been established and is materials of this framework-type are designated as CHA.

In its calcined form, the high silica CHA-type molecular sieve produced by the method of the present invention has an X-ray diffraction pattern having the characteristic lines shown in Table 1 below:

TABLE 1

| d(A) | Relative Intensities 100 I/Io |
|---|---|
| 9.36–8.98 | 80–100 |
| 6.86–6.66 | 20–60 |
| 6.33–6.15 | 0–10 |
| 5.51–5.38 | 5–40 |
| 4.97–4.86 | 5–50 |
| 4.63–4.54 | 0–10 |
| 4.28–4.20 | 20–60 |
| 3.94–3.87 | 0–10 |
| 3.83–3.76 | 0–10 |
| 3.54–3.49 | 5–40 |
| 3.41–3.36 | 5–40 |
| 3.14–3.10 | 0–10 |
| 2.889–2.853 | 5–50 |
| 2.850–2.815 | 5–40 |
| 2.650–2.620 | 0–10 |
| 2.570–2.542 | 0–10 |
| 2.467–2.441 | 0–10 |
| 2.244–2.223 | 0–10 |
| 2.088–2.070 | 0–10 |
| 2.059–2.041 | 0–10 |
| 1.883–1.869 | 0–10 |
| 1.842–1.828 | 0–10 |

These X-ray diffraction data were collected with a Philips powder X-Ray Diffractometer, equipped with a scintillation detector with graphite monochromator, using copper K-alpha radiation. The diffraction data were recorded by step-scanning at 0.02 degrees of two-theta, where theta is the Bragg angle, and a counting time of 1 second for each step. The interplanar spacing, d's, were calculated in Angstrom units, and the relative intensities of the lines, (where $I/I_0$ is one-hundredth of the intensity of the strongest line), above background were determined by integrating the peak intensities. It should be understood that diffraction data listed for this sample as single lines may consist of multiple overlapping lines which under certain conditions, such as differences in crystallographic changes, may appear as resolved or partially resolved lines. Typically, crystallographic changes can include minor changes in unit cell parameters and/or a change in crystal symmetry, without a change in the framework atom connectivities. These minor effects, including changes in relative intensities, can also occur as a result of differences in cation content, framework composition, nature and degree of pore filling, crystal size and shape, preferred orientation and thermal and/or hydrothermal history.

The CHA framework-type molecular sieve of the present invention has a composition, in its calcined and anhydrous form, involving the molar relationship:

$$(n)X_2O_3:YO_2,$$

wherein X (if present) is a trivalent element, such as aluminum, boron, iron, indium, gallium or a combination thereof, typically aluminum; Y is a tetravalent element, such as silicon, tin, titanium, germanium or a combination thereof, typically silicon; and n is from 0 to about 0.01, for example from about 0.0005 to about 0.007, such as from about 0.0008 to about 0.005. Where a halide-containing compound has been used in the synthesis of the material, the calcined form of the AEI framework-type crystalline material of the present invention is normally found to contain trace amounts, typically from about 1 to about 100 ppm, for example from about 5 to about 50 ppm, such as from about 10 to about 20 ppm, by weight of the halide, preferably fluoride.

In one embodiment, the CHA framework-type crystalline material of the present invention is substantially free of framework phosphorus.

Typically, the CHA framework-type crystalline material of the present invention is produced as crystals having an average diameter less than or equal to 4 micron, such as from about 0.5 to about 4 micron. Moreover, in some cases, particularly where the material is produced in the presence of colloidal LEV seeds, the CHA framework-type crystalline material of the present invention is produced as crystals having a twinned morphology.

In its as-synthesized form, the CHA framework-type molecular sieve of the present invention has a composition involving the molar relationship:

$$(n)X_2O_3:YO_2:(m)R:(x)F:z\ H_2O,$$

wherein X, Y and n are as defined in the preceding paragraph, R is at least one organic directing agent and wherein m ranges from about 0.01 to about 2, such as from about 0.1 to about 1, z ranges from about 0.5 to about 100, such as from about 2 to about 20 and x ranges from about 0 to about 2, such as from about 0.01 to about 1. The R and F components, which are associated with the material as a result of their presence during crystallization, are at least partly removed by post-crystallization methods hereinafter more particularly described. Typically, the as-synthesized CHA framework-type crystalline material of the present invention contains only low levels of alkali metal, generally such that the combined amount of any potassium and sodium is less than 50% of the $X_2O_3$ on a molar basis. For this reason, after removal of the organic directing agent (R), the material generally exhibits catalytic activity without a preliminary ion-exchange step to remove alkali metal cations.

To the extent desired and depending on the $X_2O_3/YO_2$ molar ratio of the material, any cations in the as-synthesized CHA framework-type material can be replaced in accordance with techniques well known in the art, at least in part, by ion exchange with other cations. Preferred replacing cations include metal ions, hydrogen ions, hydrogen precursor, e.g., ammonium ions, and mixtures thereof. Particularly preferred cations are those which tailor the catalytic activity for certain hydrocarbon conversion reactions. These include hydrogen, rare earth metals and metals of Groups IIA, IIIA, IVA, VA, IB, IIB, IIIB, IVB, VB, VIIB, VIIB and VIII of the Periodic Table of the Elements.

The CHA framework-type molecular sieve of the invention can be prepared from a reaction mixture containing a source of water, a source of an oxide of the tetravalent element Y, optionally a source of an oxide of the trivalent element X, at least one organic directing agent (R) as described below, seeds of a molecular sieve having a framework-type other than CHA, and preferably an AEI framework-type material, and typically a halide or a halide-containing compound, such as a fluoride or a fluoride-containing compound, said reaction mixture having a composition, in terms of mole ratios of oxides, within the following ranges:

| Reactants | Useful | Typical |
| --- | --- | --- |
| $H_2O/YO_2$ | 0.1 to 20 | 2 to 10 |
| Halide/$YO_2$ | 0 to 2 | 0.01 to 1 |
| R/$YO_2$ | 0.01 to 2 | 0.1 to 1 |
| $X_2O_3/YO_2$ | 0 to 0.1 | 0 to 0.01 |

Where the tetravalent element Y is silicon, suitable sources of silicon include silicates, e.g., tetraalkyl orthosilicates, fumed silica, such as Aerosil (available from Degussa), and aqueous colloidal suspensions of silica, for example that sold by E.I. du Pont de Nemours under the tradename Ludox. Where the trivalent element X is aluminum, suitable sources of aluminum include aluminum salts, especially water-soluble salts, such as aluminum nitrate, as well as hydrated aluminum oxides, such as boehmite and pseudoboehmite. Where the halide is fluoride, suitable sources of fluoride include hydrogen fluoride, although more benign sources of fluoride such as alkali metal fluorides and fluoride salts of the organic directing agent are preferred.

The organic directing agent R used herein conveniently comprises a multi-cyclic amine or ammonium compound. Conveniently, the multi-cyclic amine or ammonium compound comprises a tricyclic or tetracyclic amine or ammonium compound, such as an N-alkyl-3-quinuclidinol, an N,N,N-tri-alkyl-1-adamantylammonium compound, an N,N,N-trialkyl-exoaminonorbornane or a combination thereof, such as an N,N,N-trimethyl-1-adamantylammonium compound. Suitable compounds include hydroxides and salts, such as halides.

The amount of seeds employed can vary widely, but generally the reaction mixture comprises from about 0.1 ppm by weight to about 10,000 ppm by weight, such as from about 100 ppm by weight to about 5,000 by weight, of said seeds. The seeds comprise a material having a framework-type other than CHA, such as an LEV, OFF or AEI framework-type molecular sieve. The seeds may be added to the reaction mixture as a colloidal suspension in a liquid medium, such as water. The production of colloidal seed suspensions and their use in the synthesis of molecular sieves are disclosed in, for example, International Publication Nos. WO 00/06493 and WO 00/06494 published on Feb. 10, 2000 and incorporated herein by reference. Preferably, the seeds are of the AEI framework-type material and particularly a silicate or aluminosilicate of the AEI structure.

Conveniently, the reaction mixture has a pH of about 4 to about 14, such as about 4 to about 10, for example about 6 to about 8.

Crystallization can be carried out at either static or stirred conditions in a suitable reactor vessel, such as for example, polypropylene jars or Teflon®-lined or stainless steel autoclaves, at a temperature of about 50° C. to about 300° C., such as about 135° C. to about 175° C., for a time sufficient for crystallization to occur. Formation of the crystalline product can take anywhere from around 30 minutes up to as much as 2 weeks, such as from about 45 minutes to about 240 hours, for example from about 1.0 to about 120 hours. The duration depends on the temperature employed, with higher temperatures typically requiring shorter hydrothermal treatments.

Typically, the crystalline product is formed in solution and can be recovered by standard means, such as by centrifugation or filtration. The separated product can also be washed, recovered by centrifugation or filtration and dried. The resultant product is found to comprise particles with an average crystal size below 4 microns, such as below 2 microns and typically about 1 micron.

As a result of the crystallization process, the recovered crystalline product contains within its pores at least a portion of the organic directing agent used in the synthesis. In a preferred embodiment, activation is performed in such a manner that the organic directing agent is removed from the molecular sieve, leaving active catalytic sites within the microporous channels of the molecular sieve open for contact with a feedstock. The activation process is typically accomplished by calcining, or essentially heating the molecular sieve comprising the template at a temperature of from about 200° C. to about 800° C. in the presence of an oxygen-containing gas. In some cases, it may be desirable to heat the molecular sieve in an environment having a low or zero oxygen concentration. This type of process can be used for partial or complete removal of the organic directing agent from the intracrystalline pore system. In other cases, particularly with smaller organic directing agents, complete or partial removal from the sieve can be accomplished by conventional desorption processes.

Once the CHA framework-type material of the invention has been synthesized, it can be formulated into a catalyst composition by combination with other materials, such as binders and/or matrix materials, that provide additional hardness or catalytic activity to the finished catalyst.

Materials which can be blended with the CHA framework-type material of the invention can be various inert or catalytically active materials. These materials include compositions such as kaolin and other clays, various forms of rare earth metals, other non-zeolite catalyst components, zeolite catalyst components, alumina or alumina sol, titania, zirconia, quartz, silica or silica sol, and mixtures thereof. These components are also effective in reducing overall catalyst cost, acting as a thermal sink to assist in heat shielding the catalyst during regeneration, densifying the catalyst and increasing catalyst strength. When blended with such components, the amount of zeolitic material contained in the final catalyst product ranges from 10 to 90 weight percent of the total catalyst, preferably 20 to 70 weight percent of the total catalyst.

The CHA framework-type crystalline material described herein can be used to dry gases and liquids; for selective molecular separation based on size and polar properties; as an ion-exchanger; as a chemical carrier; in gas chromatography; and as a catalyst in organic conversion reactions. Examples of suitable catalytic uses of the CHA framework-type crystalline material described herein include (a) hydrocracking of heavy petroleum residual feedstocks, cyclic stocks and other hydrocrackate charge stocks, normally in the presence of a hydrogenation component iselected from Groups 6 and 8 to 10 of the Periodic Table of Elements; (b) dewaxing, including isomerization dewaxing, to selectively remove straight chain paraffins from hydrocarbon feedstocks typically boiling above 177° C., including raffinates and lubricating oil basestocks; (c) catalytic cracking of hydrocarbon feedstocks, such as naphthas, gas oils and residual oils, normally in the presence of a large pore cracking catalyst, such as zeolite Y; (d) oligomerization of straight and branched chain olefins having from about 2 to 21, preferably 2 to 5 carbon atoms, to produce medium to heavy olefins which are useful for both fuels, i.e., gasoline or a gasoline blending stock, and chemicals; (e) isomerization of olefins, particularly olefins having 4 to 6 carbon atoms, and especially normal butene to produce iso-olefins; (f) upgrading of lower alkanes, such as methane, to higher hydrocarbons, such as ethylene and benzene; (g) disproportionation of alkylaromatic hydrocarbons, such as toluene, to produce dialkylaromatic hydrocarbons, such as xylenes; (h) alkylation of aromatic hydrocarbons, such as benzene, with olefins, such as ethylene and propylene, to produce ethylbenzene and cumene; (i) isomerization of dialkylaromatic hydrocarbons, such as xylenes, (j) catalytic reduction of nitrogen oxides and (k) synthesis of monoalkylamines and dialkylamines.

In particular, the CHA framework-type material described herein is useful in the catalytic conversion of oxygenates to one or more olefins, particularly ethylene and propylene. As used herein, the term "oxygenates" is defined to include, but is not necessarily limited to aliphatic alcohols, ethers, carbonyl compounds (aldehydes, ketones, carboxylic acids, carbonates, and the like), and also compounds containing hetero-atoms, such as, halides, mercaptans, sulfides, amines, and mixtures thereof. The aliphatic moiety will normally contain from about 1 to about 10 carbon atoms, such as from about 1 to about 4 carbon atoms.

Representative oxygenates include lower straight chain or branched aliphatic alcohols, their unsaturated counterparts, and their nitrogen, halogen and sulfur analogues. Examples of suitable oxygenate compounds include methanol; ethanol; n-propanol; isopropanol; $C_4$–$C_{10}$ alcohols; methyl ethyl ether; dimethyl ether; diethyl ether; di-isopropyl ether; methyl mercaptan; methyl sulfide; methyl amine; ethyl mercaptan; di-ethyl sulfide; di-ethyl amine; ethyl chloride; formaldehyde; di-methyl carbonate; di-methyl ketone; acetic acid; n-alkyl amines, n-alkyl halides, n-alkyl sulfides having n-alkyl groups of comprising the range of from about 3 to about 10 carbon atoms; and mixtures thereof. Particularly suitable oxygenate compounds are methanol, dimethyl ether, or mixtures thereof, most preferably methanol. As used herein, the term "oxygenate" designates only the organic material used as the feed. The total charge of feed to the reaction zone may contain additional compounds, such as diluents.

In the present oxygenate conversion process, a feedstock comprising an organic oxygenate, optionally with one or more diluents, is contacted in the vapor phase in a reaction zone with a catalyst comprising the molecular sieve of the present invention at effective process conditions so as to produce the desired olefins. Alternatively, the process may be carried out in a liquid or a mixed vapor/liquid phase. When the process is carried out in the liquid phase or a mixed vapor/liquid phase, different conversion rates and selectivities of feedstock-to-product may result depending upon the catalyst and the reaction conditions.

When present, the diluent(s) is generally non-reactive to the feedstock or molecular sieve catalyst composition and is typically used to reduce the concentration of the oxygenate in the feedstock. Non-limiting examples of suitable diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. Diluent(s) may comprise from about 1 mol % to about 99 mol % of the total feed mixture.

The temperature employed in the oxygenate conversion process may vary over a wide range, such as from about 200° C. to about 1000° C., for example from about 250° C. to about 800° C., including from about 250° C. to about 750° C., conveniently from about 300° C. to about 650° C., typically from about 350° C. to about 600° C. and particularly from about 400° C. to about 600° C.

Light olefin products will form, although not necessarily in optimum amounts, at a wide range of pressures, including but not limited to autogenous pressures and pressures in the range of from about 0.1 kPa to about 10 MPa. Conveniently, the pressure is in the range of from about 7 kPa to about 5 MPa, such as in the range of from about 50 kPa to about 1 MPa. The foregoing pressures are exclusive of diluent, if any is present, and refer to the partial pressure of the feedstock as it relates to oxygenate compounds and/or mixtures thereof. Lower and upper extremes of pressure may adversely affect selectivity, conversion, coking rate, and/or reaction rate; however, light olefins such as ethylene still may form.

The process should be continued for a period of time sufficient to produce the desired olefin products. The reaction time may vary from tenths of seconds to a number of hours. The reaction time is largely determined by the reaction temperature, the pressure, the catalyst selected, the weight hourly space velocity, the phase (liquid or vapor) and the selected process design characteristics.

A wide range of weight hourly space velocities (WHSV) for the feedstock will function in the present process. WHSV is defined as weight of feed (excluding diluent) per hour per weight of a total reaction volume of molecular sieve catalyst (excluding inerts and/or fillers). The WHSV generally should be in the range of from about 0.01 $hr^{-1}$ to about 500 $hr^{-1}$, such as in the range of from about 0.5 $hr^{-1}$ to about 300 $hr^{-1}$, for example in the range of from about 0.1 $hr^{-1}$ to about 200 $hr^{-1}$.

A practical embodiment of a reactor system for the oxygenate conversion process is a circulating fluid bed reactor with continuous regeneration, similar to a modern fluid catalytic cracker. Fixed beds are generally not preferred for the process because oxygenate to olefin conversion is a highly exothermic process which requires several stages with intercoolers or other cooling devices. The reaction also results in a high pressure drop due to the production of low pressure, low density gas.

Because the catalyst must be regenerated frequently, the reactor should allow easy removal of a portion of the catalyst to a regenerator, where the catalyst is subjected to a regeneration medium, such as a gas comprising oxygen, for example air, to burn off coke from the catalyst, which restores the catalyst activity. The conditions of temperature, oxygen partial pressure, and residence time in the regenerator should be selected to achieve a coke content on regenerated catalyst of less than about 0.5 wt %. At least a portion of the regenerated catalyst should be returned to the reactor.

In one embodiment, the catalyst is pretreated with dimethyl ether, a $C_2$–$C_4$ aldehyde composition and/or a $C_4$–$C_7$ olefin composition to form an integrated hydrocarbon co-catalyst within the porous framework of the CHA framework-type molecular sieve prior to the catalyst being used to convert oxygenate to olefins. Desirably, the pretreatment is conducted at a temperature of at least 10° C., such as at least 25° C., for example at least 50° C., higher than the temperature used for the oxygenate reaction zone and is arranged to produce at least 0.1 wt %, such as at least 1 wt %, for example at least about 5 wt % of the integrated hydrocarbon co-catalyst, based on total weight of the molecular sieve. Such preliminary treating to increase the carbon content of the molecular sieve is known as "pre-pooling" and is further described in U.S. application Ser. Nos. 10/712,668, 10/712,952 and 10/712,953 all of which were filed Nov. 12, 2003 and are incorporated herein by reference.

The invention will now be more particularly described with reference to the following Examples and the accompanying drawings.

EXAMPLE 1

0.818 ml of a 23.5 mg/ml aqueous solution of Al(NO$_3$)$_3$·9H$_2$O was added to 15.674 ml of a 0.5721 molar aqueous solution of N,N,N-trimethyl-1-adamantylammonium hydroxide (TMAA$^+$ OH$^-$) followed by 4.00 ml of tetraethylorthosilicate. The resultant mixture was continuously stirred in a sealed container overnight at room temperature until all the tetraethylorthosilicate was completely hydrolyzed. To the resultant clear solution was added 0.390 ml of a 48 wt % aqueous solution of hydrofluoric acid which immediately resulted in the production of a slurry. This slurry was further homogenized by stirring and exposure to air for evaporation of water and ethanol until a thick slurry mixture was obtained. Extra water was further evaporated from the slurry mixture under static conditions to give 4650 mg of a dry gel solid having the following molar composition:

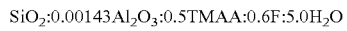

SiO$_2$:0.00143Al$_2$O$_3$:0.5TMAA:0.6F:5.0H$_2$O

The resultant solid was divided into 2 approximately equal parts. To one part was added with mechanical mixing 4 mg (0.2 wt % based on the dry gel solid) of a seeding material, AEI having a Si/Al atomic ratio of 8.9 and Si/Na atomic ratio of 26.4, whereas no seeds were added to the other part. Each solid was then transferred to a respective Teflon®-lined 5 ml pressure reactor and crystallized at 150° C. for 65 hours under slow rotation (about 60 rpm). After cooling, each product was recovered by centrifuging, washed with distilled water, and dried at 100° C. to give 598 mg of a white microcrystalline solid for the seeded synthesis and 701 mg of a white microcrystalline solid for the unseeded synthesis.

Figure 2:
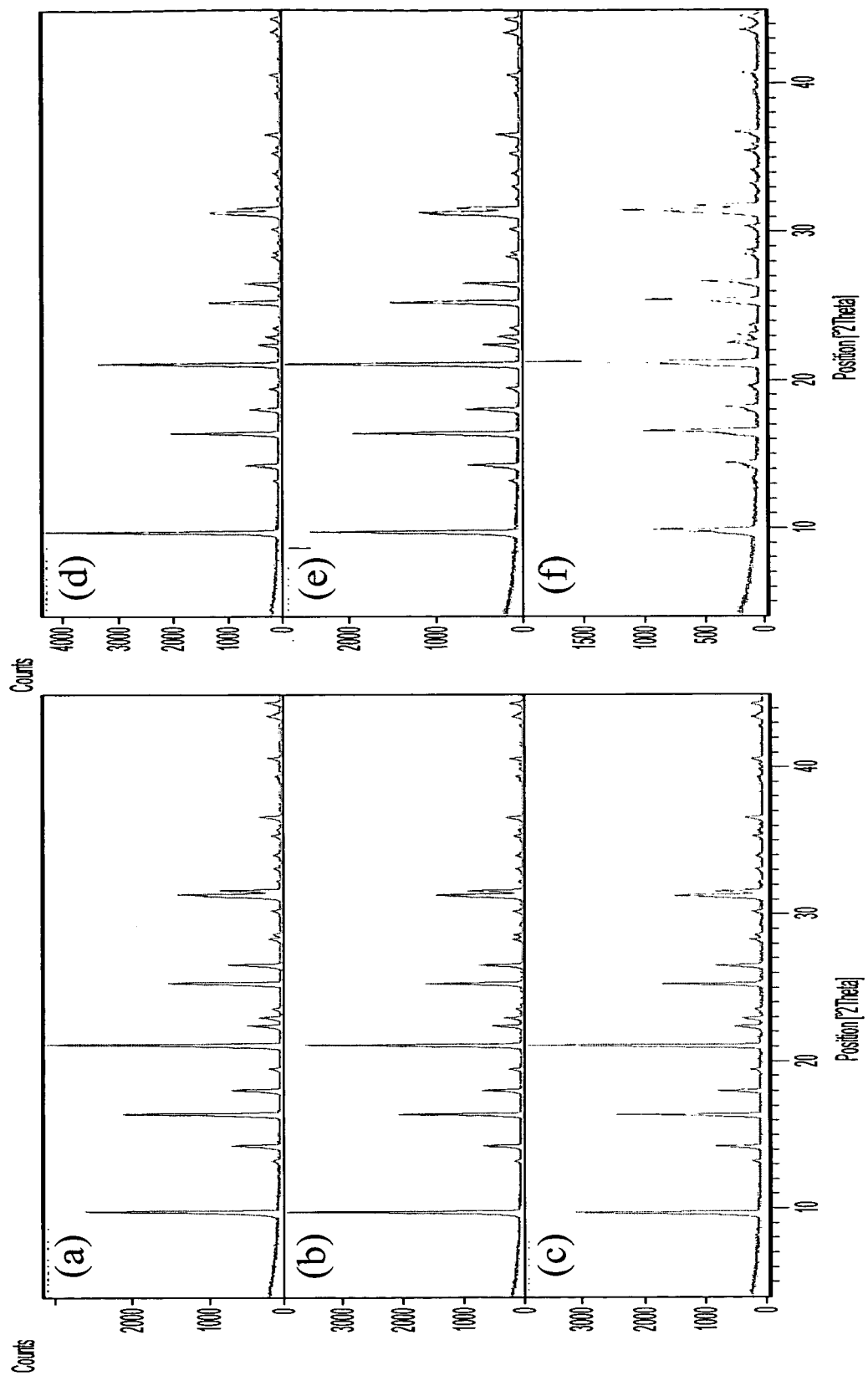
FIGS. 2(a) to 2(f) are X-ray diffraction patterns of the as-synthesized products of the unseeded syntheses of Examples 1 to 6 respectively.
Figure 3:
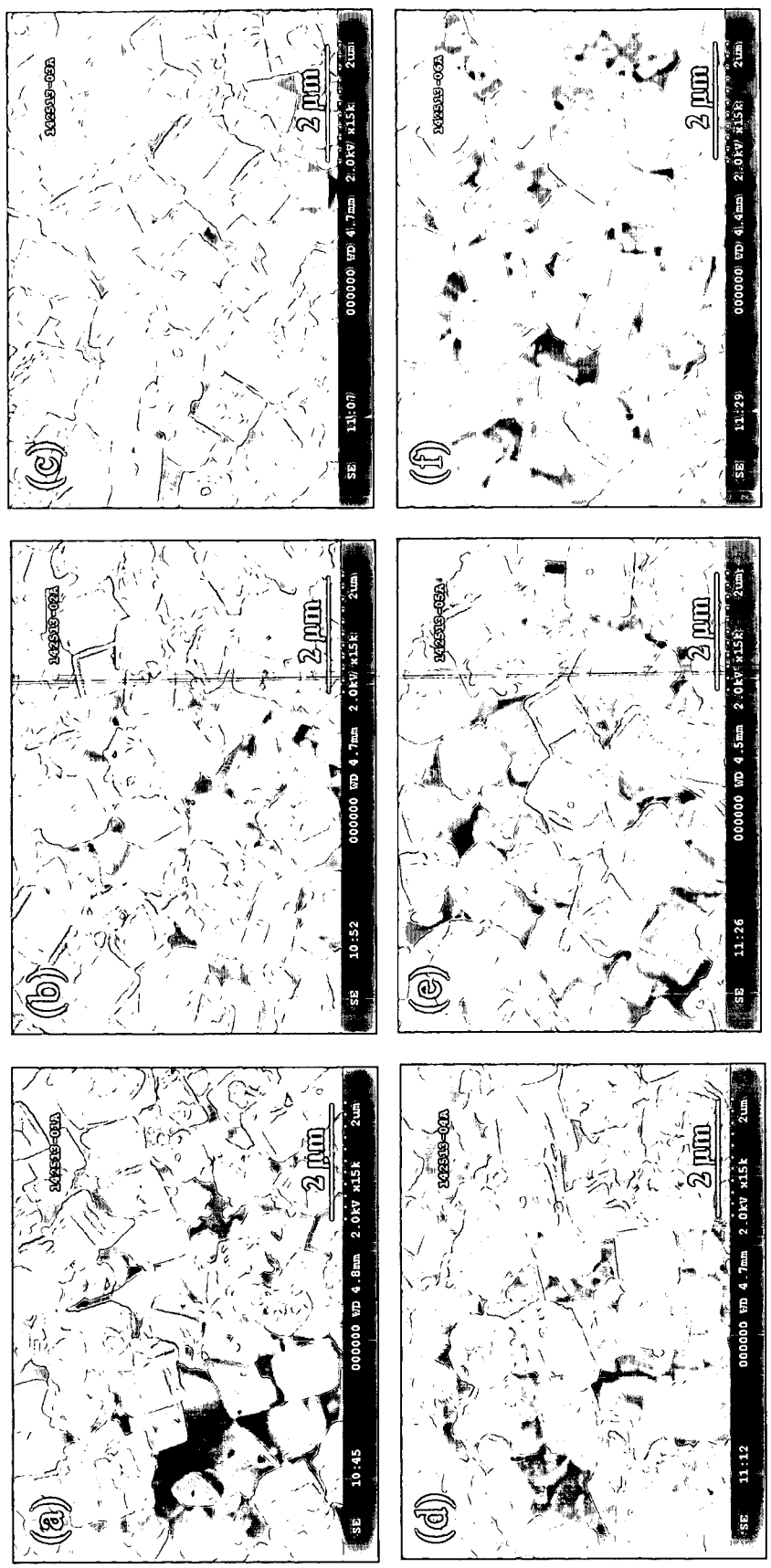
FIGS. 3(a) to 3(f) are SEM pictures of the products of the seeded syntheses of Examples 1 to 6 respectively.
Figure 4:
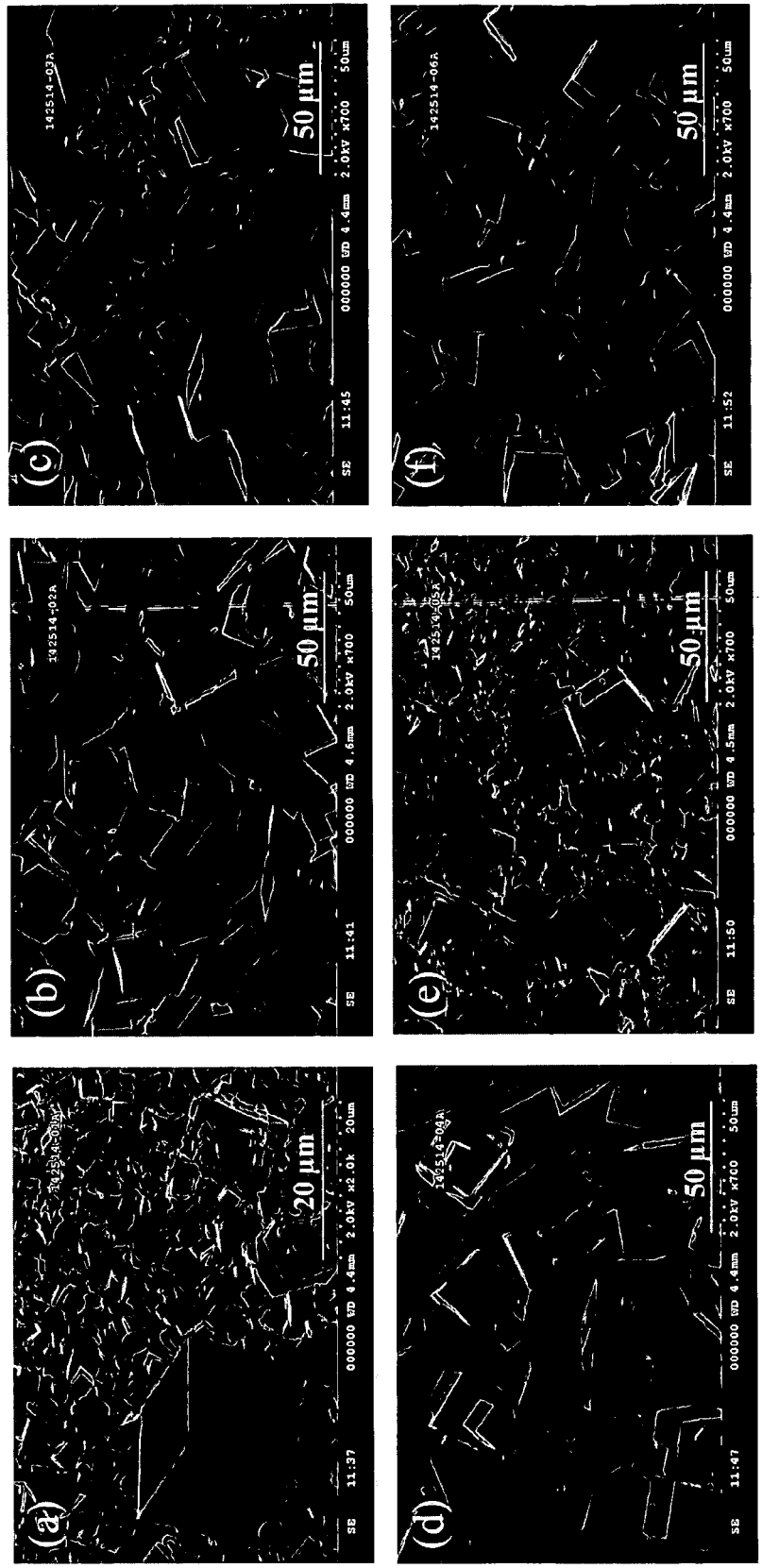
FIGS. 4(a) to 4(f) are SEM pictures of the products of the unseeded syntheses of Examples 1 to 6 respectively.
Figure 5:
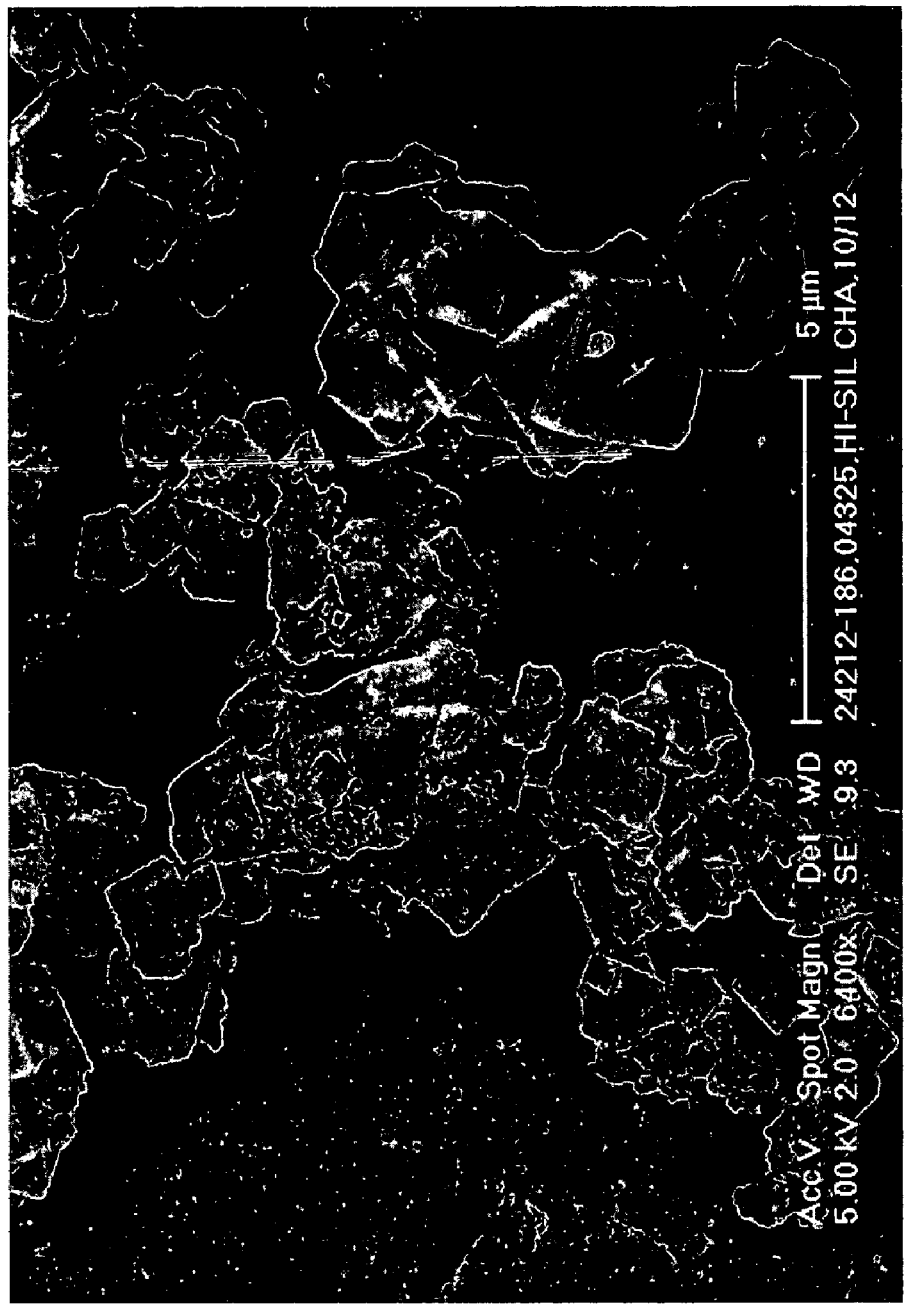
FIG. 5 is an SEM picture of the products of the Example 9.

The as-synthesized products of the seeded and unseeded processes had the X-ray diffraction patterns shown in FIGS. 1(a) and 2(a) respectively demonstrating that both products had a CHA structure. The silica to alumina molar ratio of each product was found to be about 700. The results of SEM analysis are shown in FIG. 3(a) for the seeded synthesis and FIG. 4(a) for the non-seeded synthesis. From these results it will be seen that the seeded synthesis gave a product with a substantially uniform particle size of about 1 micron and a cubic morphology, although some defects and irregular crystals were observed. However, the non-seeded system produced significantly larger particles, with a size up to 20 microns, as well as producing bimodal particle size distributions.

EXAMPLE 2

The process of Example 1 was repeated but with the amount of the 23.5 mg/ml aqueous solution of Al(NO$_3$)$_3$·9H$_2$O being decreased to 0.716 ml to give, after evaporation of water and ethanol, 4648 mg of a dry gel solid having the following molar composition:

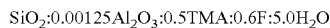

SiO$_2$:0.00125Al$_2$O$_3$:0.5TMA:0.6F:5.0H$_2$O

After dividing the dry gel solid into 2 equal parts and adding 0.2 wt % of the AEI seeds to only one part, the solids were crystallized as in Example 1 to give, after washing and drying, 686 mg of a white microcrystalline solid for the seeded synthesis and 566 mg of a white microcrystalline solid for the unseeded synthesis.

The as-synthesized products of the seeded and unseeded processes had the X-ray diffraction patterns shown in FIGS. 1(b) and 2(b) respectively demonstrating that both products had a CHA structure. The silica to alumina molar ratio of each product was found to be about 800. The results of SEM analysis are shown in FIG. 3(b) for the seeded synthesis and FIG. 4(b) for the non-seeded synthesis. Again it will be seen that the seeded synthesis gave a product with a substantially uniform particle size of about 1 micron and a cubic morphology, the non-seeded system produced significantly larger particles, with a size up to 20 microns.

EXAMPLES 3 TO 6

The process of Example 1 was repeated but with the amount of the 23.5 mg/ml aqueous solution of Al(NO$_3$)$_3$·9H$_2$O being decreased to 0.636 ml (Example 3), 0.572 ml (Example 4), 0.520 ml (Example 5) and 0.478 ml (Example 6) to give, after evaporation of water and ethanol, 4646 mg, 4646 mg 4644 mg and 4644 mg, respectively, of dry gel solids having the following molar compositions:

SiO$_2$:0.0011Al$_2$O$_3$:0.5TMA:0.6F:5.0H$_2$O      Example 3

SiO$_2$:0.00100Al$_2$O$_3$:0.5TMA:0.6F:5.0H$_2$O      Example 4

SiO$_2$:0.00091Al$_2$O$_3$:0.5TMA:0.6F:5.0H$_2$O      Example 5

SiO$_2$:0.00083Al$_2$O$_3$:0.5TMA:0.6F:5.0H$_2$O      Example 6

As before, each dry gel solid was divided into 2 equal parts and the parts separately crystallized as described in Example 1 with only one of the parts containing 0.2 wt % of the AEI seeds. The results of the syntheses are summarized in Table 2.

TABLE 2

| Example | Seeded Synthesis | | Non-seeded Synthesis | |
| --- | --- | --- | --- | --- |
| | Yield (mg) | Si/Al$_2$ | Yield (mg) | Si/Al$_2$ |
| 3 | 669 | 900 | 594 | 900 |
| 4 | 647 | 1000 | 601 | 1000 |
| 5 | 643 | 1100 | 645 | 1100 |
| 6 | 650 | 1200 | 605 | 1200 |

X-ray diffraction patterns for the products of the seeded syntheses of Examples 3 to 6 are shown in FIGS. 1(c) to 1(f) respectively and for the products of the unseeded syntheses are shown in FIGS. 2(c) to 2(f) respectively. SEM results for the products of the seeded syntheses of Examples 3 to 6 are shown in FIGS. 3(c) to 3(f) respectively and for the products of the unseeded syntheses are shown in FIGS. 4(c) to 4(f) respectively.

EXAMPLE 7

The as-synthesized material from the seeded synthesis of Example 1 was pressed to a pellet at 30000 psig (2.07×10$^5$ kPa) and then ground and sieved to between 80 and 125 μm. Two separate samples of the sized material were weighed between 21 and 22 mg and mixed separately with 90 mg of 100 μm silicon carbide. These mixtures were loaded into separate 1.9 mm internal diameter tubes sealed at the bottom with a quartz frit. The tubes were sealed into heated reactor blocks and the catalysts were then calcined at 540° C. under flowing air for 2 hours to effect organic template removal. The calcined catalysts were then subjected to a mixture of 85% methanol in $N_2$ at 540° C., approximately 100 weight hourly space velocity (WHSV), and 40 psia (276 kPa) methanol partial pressure for 6 minutes. During the methanol reaction, the reactor effluents were collected and stored at timed intervals for analysis by gas chromatography. Following the methanol reaction the catalysts were subjected to a flow of 50% oxygen in nitrogen at 550° C. for approximately 90 minutes to burn off deposited coke. The reactor effluents were analyzed by infrared spectroscopy with quantitation of both carbon monoxide and carbon dioxide to determine the amounts of coke deposition.

Selectivities to hydrocarbon products were calculated. The values given below are averages of each individual selectivity over the entire reaction. Each value represents an average of the selectivities obtained from the two individual repeats.

| Product | Selectivity |
|---------|-------------|
| $C_1$ | 4.2 |
| $C_2^0$ | 0.4 |
| $C_2^-$ | 39.5 |
| $C_3^0$ | 0.3 |
| $C_3^-$ | 34.6 |
| $C_4$ | 13.9 |
| $C_5^+$ | 4.3 |
| Coke | 2.7 |

EXAMPLE 8

The as-synthesized materials for both the seeded and unseeded preparations of Example 4 were individually pressed to pellets at 30000 psig ($2.07 \times 10^5$ kPa) and then ground and sieved to between 80 and 125 µm. Two separate samples of the sized material were weighed between 21 and 22 mg and mixed separately with 90 mg of 100 µm silicon carbide. These mixtures were loaded into separate 1.9 mm internal diameter tubes sealed at the bottom with a quartz frit. The tubes were sealed into heated reactor blocks and the catalysts were then calcined at 540° C. under flowing air for 2 hours to effect organic template removal. The calcined catalysts were then subjected to a mixture of 85% methanol in $N_2$ at 540° C., approximately 100 weight hourly space velocity (WHSV), and 40 psia (276 kPa) methanol partial pressure for 6 minutes. During the methanol reaction, the reactor effluents were collected and stored at timed intervals for analysis by gas chromatography. Following the methanol reaction the catalysts were subjected to a flow of 50% oxygen in nitrogen at 550° C. for approximately 90 minutes to burn off deposited coke. The reactor effluents were analyzed by infrared spectroscopy with quantitation of both carbon monoxide and carbon dioxide to determine the amounts of coke deposition.

Selectivities to hydrocarbon products were calculated for each reaction. The values given below are averages of each individual selectivity over the entire reaction. Each value represents an average of the selectivities obtained from the two individual repeats.

| Selectivity | Seeded | Unseeded |
|-------------|--------|----------|
| $C_1$ | 4.6 | 5.6 |
| $C_2^0$ | 0.5 | 0.8 |
| $C_2^-$ | 38.2 | 38.5 |
| $C_3^0$ | 0.1 | 0.4 |
| $C_3^-$ | 35.3 | 32.9 |
| $C_4$ | 14.3 | 13.0 |
| $C_5^+$ | 4.3 | 4.3 |
| Coke | 2.6 | 4.8 |

EXAMPLE 9

The process of Example 1 was repeated but with the amount of the reagents increased by a factor of 5. After evaporation of ethanol and most of the water, a colloidal suspension of LEV seeds prepared according to WO 00/06494, published Feb. 10, 2000 (dry levynite content 11 wt %, Si/Al=7) in the amount of 0.2 wt % LEV on the basis of dry gel was added with stirring. Upon further evaporation of water a dry gel solid was obtained having the following molar composition:

$SiO_2$:(1/1200)$Al_2O_3$:0.5TMA:0.6F:5.0$H_2O$

The gel was divided into two equal portions, which were sealed into two 23 ml Teflon-lined Parr bombs and then were heated to 185° C. for 65 hours. X-ray diffraction indicated that the solid product was pure chabazite, and elemental analysis showed that the chabazite had Si/Al atomic ratio of 228.

The scanning electron micrograph (SEM) of the resultant product is shown in Figure micrograph show that a majority of the high silica chabazite crystals were twinned. While the present invention has been described and illustrated by reference to particular embodiments, those of ordinary skill in the art will appreciate that the invention lends itself to variations not necessarily illustrated herein. For this reason, then, reference should be made solely to the appended claims for purposes of determining the true scope of the present invention.

We claim:

1. A method of synthesizing a crystalline material having a CHA framework-type, the method comprising:
   a) forming a reaction mixture capable of forming said crystalline material having a CRA framework-type, wherein the reaction mixture further comprises seeds of a crystalline material comprising an AEI framework-type; and
   b) recovering from said reaction mixture said crystalline material comprising a CHA framework-type.

2. The method of claim 1 wherein said reaction mixture comprises from about 0.01 ppm by weight to about 10,000 ppm by weight of said seeds.

3. The method claim 1 wherein said reaction mixture comprises from about 100 ppm by weight to about 5,000 by weight of said seeds.

4. The method of claim 1 wherein said seeds comprise an aluminosilicate or silicate having an AEI framework-type.

5. The method of claim 1 wherein said crystalline material comprising a CHA framework-type recovered in (b) is composed of crystals having an average diameter less than or equal to 4 micron.

6. The method of claim 1 wherein said crystalline material comprising a CHA framework-type recovered in (b) is composed of crystals having an average diameter of about 0.5 to about 4 micron.

7. A method of synthesizing a crystalline material having a CHA framework-type and having, in its calcined and anhydrous form, a composition involving the molar relationship:

(n)$X_2O_3$:$YO_2$, wherein X is a trivalent element; Y is a tetravalent element, and n is from 0 to less than 0.01, the method comprising:
   (a) preparing a reaction mixture capable of forming said crystalline material having a CHA framework-type, said reaction mixture comprising a source of water, a source of an oxide of the tetravalent element Y, optionally a source of an oxide of the trivalent element X, an organic directing agent for directing the formation of said crystalline material having a CHA framework-type and seeds of a crystalline material having a framework-type other than CHA, (b) maintaining said reaction mixture under conditions sufficient to form crystals of said crystalline material having a CHA framework-type; and (c) recovering said crystalline material from (b).

8. The method of claim 7 wherein said organic directing agent comprises a multi-cyclic amine or aznmonxum compound.

9. The method of claim 8 wherein the multi-cyclic amine or ammonium compound comprises a tricycle or tetracyclic amine or animonium compound.

10. The method of claim 7 wherein said organic directing agent is an N-alkyl-3-quinuclidinol, an N,N,N-tri-alkyl-1-adarnantylammoniam compound, an N,N,N-trialkyl-exoaminonorbornane or a combination thereof.

11. The method of claim 7 wherein said organic directing agent comprises an N,N,N-trirnethyl-1-adamantylamnionium compound.

12. The method of claim 7 wherein said reaction mixture comprises from about 0.01 ppm by weight to about 10,000 ppm by weight of said seeds.

13. The method of claim 7 wherein said reaction mixture comprises from about 100 ppm by weight to about 5,000 by weight of said seeds.

14. The method of claim 7 wherein seeds comprise a crystalline material having an AEI, LEV or OFF framework-type.

15. The method of claim 7 wherein said seeds comprise an aluminosilicate or silicate having an AEI framework-type.

16. The method of claim 7 wherein said seeds are added to said reaction mixture as a colloidal suspension in a liquid medium.

17. The method of claim 7 wherein said reaction mixture also comprises a halide or a halide-containing compound.

18. The method of claim 7 wherein said reaction mixture also comprises a fluoride or fluoride-containing compound.

19. The method of claim 7 wherein said reaction mixture has a pH of about 4 to about 10.

20. The method of claim 7 wherein n is from about 0.0005 to about 0.007.

21. The method of claim 7 wherein n is from about 0.0008 to about 0.005.

22. The method of claim 7 wherein said reaction mixture has the following molar composition

| | |
|---|---|
| $H_2O/YO_2$ | 0.1 to 20 |
| Halide/$YO_2$ | 0 to 2 |
| R/$YO_2$ | 0.01 to 2; |
| $X_2O_3/YO_2$ | 0 to 0.1, | where R is said organic directing agent.

23. The method of claim 7 wherein said reaction mixture has the following molar composition

| | |
|---|---|
| $H_2O/YO_2$ | 2 to 10; |
| Halide/$YO_2$ | 0.01 to 1; |
| R/$YO_2$ | 0.1 to 1; |
| $X_2O_3/YO_2$ | 0 to 0.01, | where R is said organic directing agent.

24. The niethod of claim 7 wherein X is aluminum, boron, iron, indium, gallium or a combination thereof.

25. The method of claim 7 wherein y is silicon, tin, titanium, germanium or a combination thereof.

26. The method of claim 7 wherein X is aluminum, boron, iron, indium, gallium or a combination thereof; and Y is silicon, tin, titanium, germanium or a combination thereof.

27. The method of claim 7 wherein Y is silicon.

28. The method of claim 27 wherein X is aluminum.

29. The method of claim 27 wherein n is zero.

30. The method of claim 7 wherein said crystalline material recovered in (c) is composed of crystals having an average diameter less than or equal to 4 micron.

31. The method of claim 7 wherein said crystalline material recovered in (c) is composed of crystals having an avenge diameter of about 0.5 to about 4 micron.

32. The method of claim 7 wherein said crystalline material having a CHA framework type is substantially free of framework phosphorus.

33. A crystalline material having a CHA framework type and having, in its calcined and anhydrous form, a composition involving the molar relationship:

$$(n)X_2O_3:YO_2,$$

wherein X is a trivalent element, Y is a tetravalent element and n is from 0 to less than 0.01, and wherein the crystals of said material have an average diameter of from about 0.5 micron to 4 micron.

34. The crystalline material of claim 33 wherein n is from about 0.0005 to about 0.007.

35. The crystalline material of claim 33 wherein n is from about 0.0008 to about 0.005.

36. The ciystalline material of claim 33 wherein X is aluminum, boron, iron, indium, gallium or a combination thereof.

37. The crystalline material of claim 33 wherein Y is silicon, tin, titanium, germanium or a combination thereof.

38. The crystalline material of claim 33 wherein said material, in its calcined form, contains from about 1 to about 100 ppm by weight of a halide.

39. The crystalline material of claim 33 wherein said material, in its calcined form, contains from about 5 to about 50 ppm by weight of a halide.

40. The crystalline material of claim 33 wherein said material, in its calcined form, contains from about 10 to about 20 ppm, by weight of a halide.

41. The crystalline material of claim 33 wherein said halide comprises fluoride.

42. The crystalline material of claim 33 wherein the crystals of said material have an average diameter of about 1 to about 4 micron.

43. The crystalline material of claim 33 wherein said material is substantially free of framework phosphorus.

44. A crystalline material having a CHA framework type and having, in its caicined and anhydrous form, a composition involving the molar relationship:

$$(n)X_2O_3:YO_{02},$$

wherein X is a trivalent element, Y is a tetravalent element and ii is from 0 to less than 0.01, and wherein the crystals of said material are twinned.

45. The crystalline material of claim 44 wherein n is from about 0.0005 to about 0.007.

46. The crystalline material of claim 44 wherein n is from about 0.0008 to about 0.005.

47. The crystalline material of claim 44 wherein X is aluminum, boron, iron, indium, gallium or a combination thereof.

48. The crystalline material of claim 44 wherein Y is silicon, tin, titanium, germanium or a combination thereof.

49. The crystalline material of claim 44 wherein said material, in its calcined form, contains from about 1 to about 100 ppm by weight of a halide.

50. The crystalline material of claim 44 wherein said material, in its calcined form, contains from about 5 to about 50 ppm by weight of a halide.

51. The crystalline material of claim 44 wherein said material, in its calcined form, contains from about 10 to about 20 ppm, by weight of a halide.

52. The crystalline material of claim 44 wherein said halide comprises fluoride.

53. The crystalline material of claim 44 wherein the crystals of said material have an average diameter of about 0.5 to about 4 micron.

54. A process for producing olefins comprising contacting an organic oxygenate compound under oxygenate conversion conditions with a catalyst comprising a crystalline material produced by the method of claim 1.

55. A process for producing olefins comprising contacting an organic oxygenate compound under oxygenate conversion conditions with a catalyst comprising a crystalline material produced by the method of claim 7.

56. A process for producing olefins comprising contacting an organic oxygenate compound under oxygenate conversion conditions with a catalyst comprising the crystalline material of claim 33.

57. A process for producing olefins comprising contacting an organic oxygenate compound under oxygenate conversion conditions with a catalyst comprising the crystalline material of claim 44.

\* \* \* \* \*

UNITED STATES PATENT AND TRADEMARK OFFICE
CERTIFICATE OF CORRECTION

| | |
|---|---|
| PATENT NO. | : 7,067,108 B2 |
| APPLICATION NO. | : 11/017092 |
| DATED | : June 27, 2006 |
| INVENTOR(S) | : Machteld M. Mertens et al. |

Page 1 of 1

It is certified that error appears in the above-identified patent and that said Letters Patent is hereby corrected as shown below:

Col. 14 line 33 claim 1, should read as follows:

1. A method of synthesizing a crystalline material having a CHA framework-type, the method comprising:

a) forming a reaction mixture capable of forming said crystalline material having a CHA framework-type, wherein the reaction mixture further comprises seeds of a crystalline material comprising an AEI framework-type; and b) recovering from said reaction mixture said crystalline material comprising a CHA framework-type.

Col. 16 line 4 claim 44, should read as follows:

44. A crystalline material having a CHA framework type and having, in its calcined and anhydrous form, a composition involving the molar relationship:

$(n)X_2O_3:YO_2$, wherein X is a trivalent element, Y is a tetravalent element and n is from 0 to less than 0.01, and wherein the crystals of said material are twinned.

Signed and Sealed this

Sixth Day of January, 2009

JON W. DUDAS
*Director of the United States Patent and Trademark Office*